US005738876A

United States Patent [19]
Enevold

[11] Patent Number: 5,738,876
[45] Date of Patent: Apr. 14, 1998

[54] METHOD OF SOLUTION OVERCOATING WITH GELLING POLYMER

[75] Inventor: Karl C. Enevold, Newark, Calif.

[73] Assignee: Metabolex, Inc., Hayward, Calif.

[21] Appl. No.: 713,138

[22] Filed: Sep. 20, 1996

Related U.S. Application Data

[63] Continuation of Ser. No. 399,698, Mar. 3, 1995, abandoned.

[51] Int. Cl.$^6$ .................................................. A61K 9/14
[52] U.S. Cl. ...................... 424/486; 424/490; 424/489; 424/488; 424/497
[58] Field of Search ........................... 424/486, 488, 424/489, 490, 497

[56] References Cited

U.S. PATENT DOCUMENTS

| | | | |
|---|---|---|---|
| 4,164,559 | 8/1979 | Miyata et al. | 424/14 |
| 4,177,038 | 12/1979 | Biebricher et al. | 8/192 |
| 4,352,883 | 10/1982 | Lim | 435/178 |
| 4,391,909 | 7/1983 | Lim | 435/178 |
| 4,407,957 | 10/1983 | Lim | 435/178 |
| 4,409,331 | 10/1983 | Lim | 435/178 |
| 4,543,332 | 9/1985 | Jao et al. | 435/180 |
| 4,592,098 | 6/1986 | Magnes | 4/508 |
| 4,663,286 | 5/1987 | Tsang et al. | 435/178 |
| 4,673,566 | 6/1987 | Goosen et al. | 424/19 |
| 4,689,293 | 8/1987 | Goosen et al. | 435/1 |
| 4,696,286 | 9/1987 | Cochrum | 128/1 |
| 4,744,933 | 5/1988 | Rha et al. | 264/4.3 |
| 4,749,620 | 6/1988 | Rha et al. | 428/402.2 |
| 4,789,550 | 12/1988 | Hommel et al. | 424/493 |
| 4,791,061 | 12/1988 | Sumino et al. | 435/178 |
| 4,798,786 | 1/1989 | Tice et al. | 435/177 |
| 4,803,168 | 2/1989 | Jarvis | 435/240.22 |
| 4,806,355 | 2/1989 | Goosen et al. | 424/424 |
| 4,824,916 | 4/1989 | Kerschner et al. | 525/420 |
| 4,902,295 | 2/1990 | Walthall et al. | 623/11 |
| 4,922,295 | 5/1990 | Walthall et al. | 623/11 |
| 4,956,128 | 9/1990 | Hommel et al. | 264/4 |
| 5,041,292 | 8/1991 | Feijen | 424/484 |
| 5,227,298 | 7/1993 | Weber et al. | 435/178 |
| 5,262,055 | 11/1993 | Bae et al. | 210/645 |
| 5,286,495 | 2/1994 | Batich et al. | 424/490 |
| 5,334,640 | 8/1994 | Desai et al. | 524/56 |
| 5,362,478 | 11/1994 | Desai et al. | 424/9 |

FOREIGN PATENT DOCUMENTS

| | | | |
|---|---|---|---|
| 173 915 | 3/1986 | European Pat. Off. . | |
| 345 886B1 | 10/1993 | European Pat. Off. | A23L 1/05 |
| 2 237574 | 8/1991 | United Kingdom | C08J 3/215 |
| 91/04318 | 4/1991 | WIPO | C12N 5/00 |
| 91/07951 | 6/1991 | WIPO | A61K 9/62 |
| 91/09119 | 6/1991 | WIPO | C12N 11/10 |
| 91/11205 | 8/1991 | WIPO | A61L 15/00 |
| 93/24077 | 6/1993 | WIPO | A61F 2/02 |
| 93/24112 | 12/1993 | WIPO | A61K 9/48 |
| 94/12161 | 6/1994 | WIPO | A61K 9/50 |
| 94/15589 | 7/1994 | WIPO | A61K 9/50 |
| 94/18954 | 9/1994 | WIPO | A61K 9/48 |
| 94/25503 | 11/1994 | WIPO | C08G 69/00 |
| 95/19430 | 7/1995 | WIPO | C12N 11/10 |

OTHER PUBLICATIONS

Sun and O'Shea, "Microencapsulation of Living Cells—Long-Term Delivery System," *J. Controlled Release*, 2:137–141 (1985).

(List continued on next page.)

*Primary Examiner*—Thurman K. Page
*Assistant Examiner*—William E. Benston, Jr.
*Attorney, Agent, or Firm*—Townsend and Townsend and Crew, LLP

[57] ABSTRACT

The present invention generally relates to novel overcoating/encapsulation processes which are carried out in solution without the use of droplet generation devices. The processes may be used in the overcoating or encapsulation of a variety of materials, such as biological material, e.g., cells, proteins, etc., as well as pharmaceuticals. Compositions prepared using the methods of the present invention may find use in pharmaceutical formulation as well as coating biological material for a number of applications, including cell culturing and transplant therapy.

15 Claims, 10 Drawing Sheets

OTHER PUBLICATIONS

Sun et al., "Microencapsulation of Living Cells—a Long-Term Delivery System," *J. Controlled Release* 2:137–141 (1985).

U.S. application No. 08/186,327 filed Jan. 24, 1994.

Abuchowski et al., "Alteration of immunological properties of bovine serum albumin by covalent attachment of polyethylene glycol," *J. Biol. Chem.* 252:3578–3581 (1977).

Brendel et al., "Improved functional survivial of human islets of langerhans in three–dimensional matrix culture," *Cell Trans.* 3:427–435 (1994).

Chao et al., "Entrapment of cultured pancreas islets in three–dimensional collagen matrices," *Cell Transplantation* 1:51–60 (1992).

Chiang et al., "Synthesis of ionic conducting interpenetrating polymer networks," *Polymer Communications* pp. 34–35 (Butterworth & Co.) 1987.

Chaikof et al., "Surface topography of crosslinked poly(ethylene oxide)/polysiloxane networks in the dry and hydrated states," *Polymer Communications* 31:182–185 (1990).

Corkhill et al., "Synthetic hydrogels: 7. High EWC semi-interpenetrating polymer networks based on cellulose esters and N–containing hydrophilic monomers," *Polymer* 31:1526–1537 (1990).

Goosen et al., *Fundamentals of Animal Cell Encapsulation and Immobilization*, Ch. 6, pp. 114–131; Ch. 8, pp. 190–193; Ch. 13, 302–307 (CRC Press (1993)).

Lim et al., "Microencapsulation of living cells and tissues," *J. Pharm. Sci.* 70:351–354 (1981).

Lim et al., "Microencapsulated islets as bioartificial endocrine pancreas," *Science* 210:908–910 (1981).

Lum et al., "Prolonged reversal of diabetic state in NOD mice by xenografts of microencapsulated rat islets," *Diabetes* 40:1511–1516 (1993).

Ohgawara et al., "Maintenance of embedded pig pancreatic pseudo–islets in a collagen gel matrix: study of the effect of hydrocortisone, a collagenase inhibitor, and nicotinamide on collagenolysis and the morphogenesis of pancreatic islet-cells in collagen gel matrix," *In Vitro Cell. Dev. Biol.* 26:348–352 (1990).

METHOD OF SOLUTION OVERCOATING WITH GELLING POLYMER

This is a Continuation of application Ser. No. 08/399,698, filed Mar. 3, 1995, now abandoned.

The present invention generally relates to novel encapsulation methods which can be carried out partially or entirely in solution. The methods generally comprise the suffusion of the particle to be coated or encapsulated with a solution of multivalent ions, followed by suspension of the suffused particles in a solution of a gelling polymer. The diffusion of the multivalent ions into the polymer solution causes a gelling of that polymer around the particle without the use of bead or droplet generating devices. Particles coated using the methods described herein will generally have more uniform coating thickness than other encapsulation methods.

BACKGROUND OF THE INVENTION

A variety of microencapsulation methods and compositions are known in the art. Encapsulation compositions and methods are primarily used in pharmaceutical formulations, for example, to mask the taste of bitter drugs, formulate prolonged dosage forms, separate incompatible materials, protect chemicals from moisture or oxidation, or modify the physical characteristics of the material for ease of handling and/or processing. Typical pharmaceutical encapsulation compositions include, e.g., gelatin, polyvinyl alcohol, ethylcellulose, cellulose acetatephthalate and styrene maleic anhydride. See, Remington's Pharmaceutical Sciences, Mack Publishing Co., Easton Pa. (1990).

Microencapsulation has also been applied in the treatment of diseases by transplant therapy. While traditional medical treatments for functional deficiencies of secretory and other biological organs have focused on replacing identified normal products of the deficient organ with natural or synthetic pharmaceutical agents, transplant therapy focuses on replacement of that function with cell or organ transplants. For example, the treatment of insulin-dependent diabetes mellitus, where the pancreatic islets of Langerhans are nonfunctional, can be carried out by replacing the normal secretion of insulin by the islets in the pancreas. Insulin may be supplied either by daily administration of synthetic or substitute animal insulin, or by transplantation of functional human or animal islets.

A number of microencapsulation methods for use in transplant therapy have focused on the use of alginate polymers to supply the encapsulation composition. Alginates are linear polymers of mannuronic and guluronic acid residues which are arranged in blocks of several adjacent guluronic acid residues forming guluronate blocks and blocks of adjacent mannuronic acid residues forming mannuronate blocks, interspersed with mixed, or heterogenous blocks of alternating guluronic and mannuronic acid residues. Generally, monovalent cation alginate salts are soluble, e.g., Na-alginate.

Divalent cations, such as $Ca^{++}$, $Ba^{++}$ or $Sr^{++}$, tend to interact with guluronate, and the cooperative binding of these cations within the guluronate blocks provides the primary intramolecular crosslinking responsible for formation of stable ion-paired alginate gels. Alginate encapsulation methods generally take advantage of the gelling of alginate in the presence of these divalent cation solutions. In particular, these methods involve the suspension of the material to be encapsulated, in a solution of a monovalent cation alginate salt, e.g., sodium. Droplets of the solution are then generated in air and collected in a solution of divalent cations, e.g., $CaCl_2$. The divalent cations interact with the alginate at the phase transition between the droplet and the divalent cation solution resulting in the formation of a stable alginate gel matrix being formed.

Although the known alginate encapsulation methods will produce alginate microcapsules, there remain a number of problems with many of these processes. These methods generally require the generation of spherical alginate droplets in air, which are then collected in a solution of divalent cations to produce the desired microcapsules. Generation of alginate droplets has previously been carried out by a number of methods. For example, droplets have been generated by extrusion of alginate through a tube by gravitational flow, into a solution of divalent cations. Similarly, electrostatic droplet generators which rely on the generation of an electrostatic differential between the alginate solution and the divalent cation solution have been described. The electrostatic differential results in the alginate solution being drawn through a tube, into the solution of divalent cations. For a general discussion of droplet generation in encapsulation processes, see, e.g., M. F. A. Goosen, Fundamentals of Animal Cell Encapsulation and Immobilization, Ch. 6, pp 114–142 (CRC Press, 1993).

Further, methods have been described wherein droplets are generated from a stream of the alginate solution using a laminar air flow extrusion device. Specifically, this device comprises a capillary tube within an outer sleeve. Air is driven through the outer sleeve and the polymer solution is flow-regulated through the inner tube. The air flow from the outer sleeve breaks up the fluid flowing from the capillary tube into small droplets. See U.S. Pat. No. 5,286,495.

Although these methods will result in the production of alginate microcapsules, there remain several additional disadvantages. First, these droplet generation methods require the use of an extraneous device, e.g., an electrostatic droplet generator or air-flow extrusion device. This may add additional, low throughput steps to a microencapsulation process, resulting in higher costs and more labor intensive processes. Further, these processes often subject the material being encapsulated to shear forces during the droplet generation step and/or at the point the droplet impacts the cationic solution which may potentially damage the material being encapsulated.

Many alginate encapsulation methods described in the art often result in the production of encapsulated compositions which are either too thin, resulting in an insufficient barrier, too thick, resulting in a lack of permeability to nutrients and/or cell products required for continued functioning of the cells, or their thickness is not uniform, which results in a lack of predictability in the functioning of the encapsulated composition. This lack of uniformity can be particularly troubling in transplantation therapies, where it may result in poor immune protection for the transplant, poor diffusion of nutrients to the transplant or poor diffusion of the desired products from the transplant. Additionally, many of these methods rely on the chance incorporation of a particle to be coated within a particular alginate droplet. As such, there is an increased potential for the generation of empty microcapsules or "blanks".

Accordingly, it would be desirable to provide encapsulation methods which result in microcapsules having uniform thickness both within a single microcapsule and from one microcapsule to another. Additionally, a method which can be carried out with a reduced number of steps, without extraneous devices, with reduced production of empty or blank microcapsules, and in solution would also be desirable. The present invention provides a remedy to these and other problems.

SUMMARY OF THE INVENTION

The present invention provides a method of coating a particle with a polymer gel. The method comprises suffusing the particle with a solution of multivalent ions and washing the particle to remove the free multivalent ions from solution. The particle is then suspended in a solution of gelling polymer, whereby the multivalent ions diffuse from the particle into the gelling polymer solution, thereby gelling the polymer on the surface of the particle. A preferred gelling polymer is alginate, and preferred multivalent ions are divalent cations.

In an additional embodiment, the particle to be coated comprises biological material, e.g., cells. The biological material may be first encapsulated in a matrix. The matrix may comprise an alginate gel, and additionally or alternatively, the matrix may comprise a layer of a crosslinked mixed functionality polymer matrix with a defined matrix porosity, e.g., a crosslinked collagen matrix coating.

DESCRIPTION OF THE PREFERRED EMBODIMENT

I. Introduction

Figure 1A:
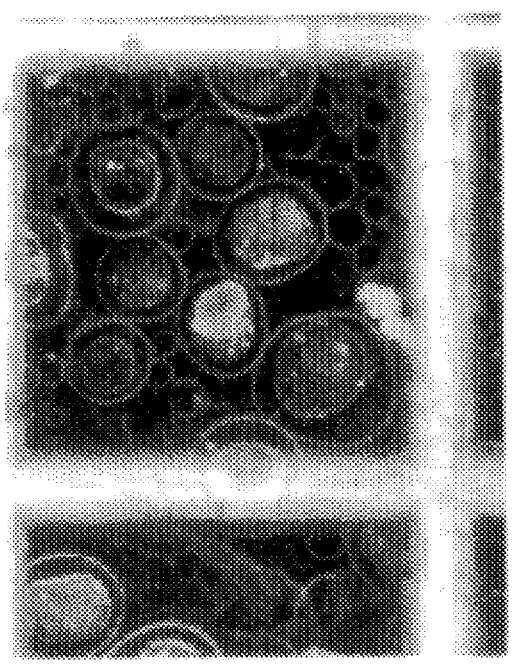
FIGS. 1A–1D shows photographs of islet cells double coated with alginate using an electrostatic ("ES") droplet generation apparatus and method for the first encapsulation and a laminar air flow extrusion apparatus for droplet generation in the second encapsulation.
Figure 1B:
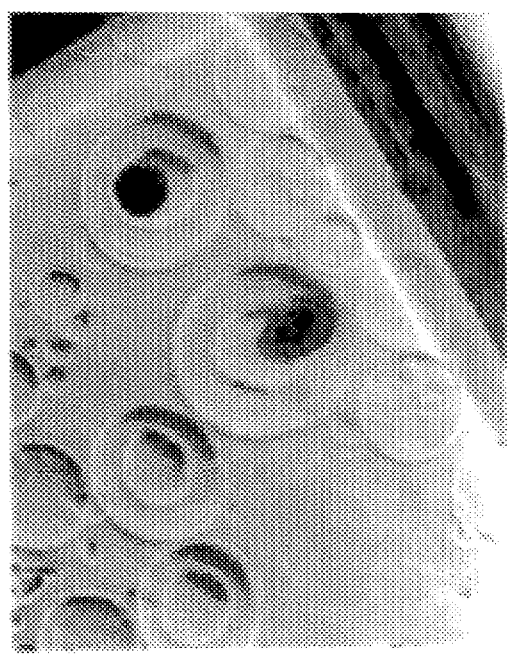
Figure 1C:
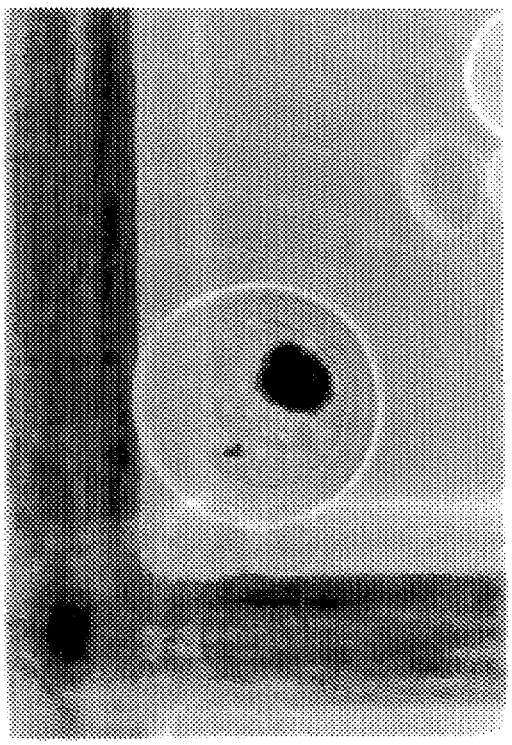
Figure 1D:
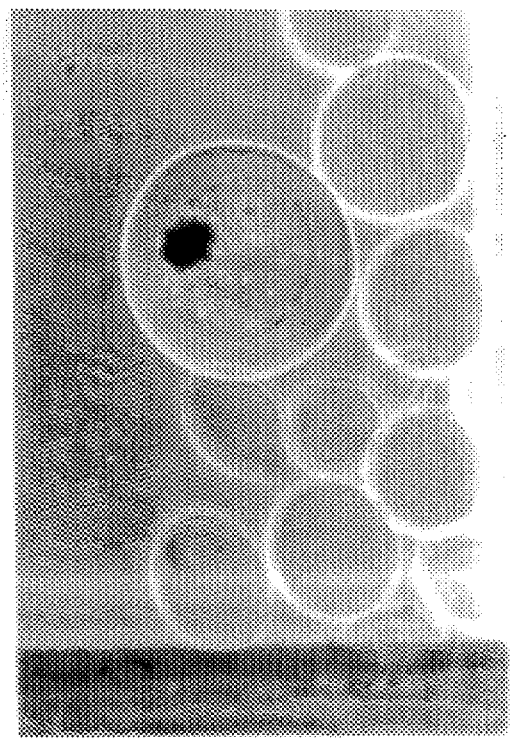

The present invention provides novel methods for encapsulating a particle in a polymer coating. The term "encapsulation" as used herein generally refers to the retention of a composition or area within a compartment, delineated by a physical barrier. For example, the encapsulated biological materials described herein, refer to biological materials which are retained within, and surrounded by a physical barrier. Thus, included within the term "encapsulation," are compositions which are coated, insofar as the coating provides a physical barrier. The term "microcapsule" as used herein, refers to an encapsulated composition, wherein the composition exists as encapsulated beads, each bead ranging in size from about 3 µm to about 2 mm in diameter. More preferably, such beads range from about 50 µm to about 300 µm in diameter. The methods of the present invention provide advantages over known encapsulation methods, in that they can be carried out in solution without the need for extraneous devices, and will result in more evenly coated particles. Further, because the overcoating process of the present invention is dependent upon the diffusion of multivalent ions from the surface of the particle to be coated, few if any blanks will be created. The methods of the present invention may be applied in preparing pharmaceutical formulations, cell culture applications, and in transplant therapy.

II. Particle Overcoating, Generally

An aspect of the present invention is to provide methods for overcoating particles with a polymer coating. "Overcoating" as the term is used herein, refers to the application of a layer of gelling polymer to a particle, such that the particle is encased by that layer. In contrast, the term "encapsulate" refers to the incorporation of a particle or particles within a gelled polymer droplet. "Solution overcoating" refers to an overcoating process which may be carried out in solution, thus requiring no droplet generation steps or devices.

"Gelling polymer" as that term is used herein, refers to a polymer which is gelled in the presence of multivalent ions. Typically, multivalent anions or cations will interact with the gelling polymer to form a stable ion pair, resulting in the gelling of the polymer. A preferred gelling polymer is alginate, which may be gelled by its interactions with divalent cations, e.g. $Ca^{+2}$, $Ba^{+2}$ and $Sr^{+2}$.

According to the methods of the present invention, particles to be coated in gelling polymer are first suffused or saturated with a solution of multivalent ions. Following the suffusion of the particle with the multivalent ion solution, the particle is washed to remove free multivalent ions from the solution as well as the surface of the particle. The particle is then suspended in a solution of the gelling polymer, whereby the multivalent ions remaining within or bound to the surface of the particle diffuse from the particle into the gelling polymer solution. Diffusion of the ions into the polymer solution results in the gelling of the polymer which surrounds the particle, such that the particle is coated with gelled polymer. Thus, the mechanism which results in the gelling of the polymer around the particle is contained on or within the particle to be coated. Specifically, the polymer gel which coats the particle is formed from the particle outward as the multivalent ions diffuse from the particle.

This is in contrast to traditional encapsulation methods which involve capturing droplets of the polymer in the gelling solution, and thus form a gel layer at the outer surface of the droplet, where it interfaces with the gelling solution, thus forming the gel layer from the outside, inward. Because encapsulation of material using this traditional method depends upon the chance incorporation of that material in a droplet, there is an increased likelihood of generating blank, or empty microcapsules, reducing the efficiency of the process.

A. Suffusion of the Particles with Multivalent Ions

Generally, the suffusion of the particles is accomplished by suspending the particles in a solution of multivalent ions for sufficient time to allow the multivalent ions to permeate and/or saturate the particle. Multivalent ions may include, e.g. divalent anions or cations, depending upon the gelling polymer used. Where the gelling polymer is an anionic polymer, e.g. alginate, divalent cations are preferred, whereas methods involving cationic gelling polymers, e.g. chitin, will generally involve the use of divalent anions, e.g. $SO_4^{-2}$. Preferred divalent cation solutions include, $CaCl_2$, $SrCl_2$ and $BaCl_2$, with $BaCl_2$ being most preferred.

The length of incubation of the particle in the multivalent ion solution will generally depend upon a number of factors, including the concentration of the multivalent ion solution, the nature of the particle to be coated and the concentration of monovalent cations in the polymer solution. Where a particle is a porous composition, permeable to the multivalent ion solution, incubation may be for a longer period. However, where the particle is impermeable to the multivalent ion solution, but is capable of retaining the divalent cations on or within its surface, the incubation time may generally be reduced. In preferred aspects, the particle is incubated in the presence of the multivalent ions for at least about 10 minutes and preferably from about 10 minutes to about 2 hours. Preferably, the particle is incubated for about 1 hour in the presence of divalent cations.

The nature of the particle to be coated may also play a role in selecting the appropriate conditions for the suffusion step. Specifically, in some aspects, the particle composition may not be amenable to extreme concentrations of divalent cations. This may be the case where the particle comprises biological material, e.g., cells, tissue fragments, or proteins which may be adversely effected by high concentrations of cationic solutions. Accordingly, the concentration of divalent cation solution may be reduced with a corresponding increase in suffusion time.

Suffusion of particles in divalent cations, for example, will typically be carried out in solutions which provide the divalent cations at a concentration greater than about 0.1 mM, and generally from about 1 mM to about 500 mM. Preferably the concentration of the divalent cation solution is from about 1 to about 50 mM. A more preferred concentration is from about 1 to about 20 mM, with from about 1 to about 5 mM being most preferred.

B. Washing the Suffused Particles

Following suffusion of the particle with the multivalent ion solution, the particle may be washed to remove any free multivalent ions which remain on the surface of the particle. The object of this first washing step is to remove unbound or free multivalent ions from the surface which may cause premature or irregular gelling of the gelling polymer. This premature gelling may result in gel formation around aggregated particles, rather than gelling around individual particles by the radial diffusion of the multivalent ions from the particle. Typically, this first wash step is carried out in a non-ionic solution, e.g., water, dextran, polyethylene glycol, sorbitol, sucrose or the like. More preferably, the wash step is carried out using a sucrose solution which is from about 5 to about 30% w/v sucrose, and most preferably, about 10%.

C. Nucleation or Coating of Particles With Gelling Polymer

Following the washing step, the suffused particles to be coated are suspended in a solution of the gelling polymer with which they will be coated. In preferred aspects, the gelling polymer used in the coating process is an anionic polymer, and more preferably, is a monovalent cation salt of alginate, e.g., sodium alginate.

Alginates are linear polymers of mannuronic and guluronic acid residues which are arranged in blocks of several adjacent guluronic acid residues forming guluronate blocks and blocks of adjacent mannuronic acid residues forming mannuronate blocks, interspersed with mixed, or heterogenous blocks of alternating guluronic and mannuronic acid residues. Generally, monovalent cation alginate salts are soluble, e.g., Na-alginate. Divalent cations, such as $Ca^{++}$, $Ba^{++}$, $Sr^{++}$ and $Fe^{++}$ tend to interact with guluronate, and the cooperative binding of these cations within the guluronate blocks provides the primary intramolecular crosslinking responsible for formation of stable alginate gels.

For certain applications it may be desirable to use alginate gels which are nonfibrogenic. This is particularly the case where the encapsulated biological material is to be implanted in a mammalian host. Fibrogenicity of alginates is generally attributed to contaminating fucan and polyphenol rich physoides and other particulate contaminants. These contaminants may be purified away from the alginate to reduce its fibrogenicity. See, e.g., Published PCT Application No. WO 93/24077.

The thickness of the coating applied to the particle will generally depend upon the particular needs of the coated material. The thickness may be varied by adjusting a number of the coating parameters. For example, a thicker coating may be applied by suffusing the particle with a higher level of multivalent ions. Alternatively, a thicker coating may be provided by allowing for greater diffusion of ions from the particle, either by prolonging the diffusion step or decreasing the tonicity of the gelling polymer solution. Likewise, a thinner coating may be achieved by making the opposite adjustments. Typically, the thickness of the coating applied using the methods of the present invention will range from about 10 µm to about 200 µm. Preferably, the coating thickness will be from about 20 to about 60 µm, and more preferably from about 30 to about 40 µm.

In preferred embodiments, the gelling polymer solution will generally be formulated whereby the rate of diffusion of the multivalent ions from the particle to be coated is enhanced. For example, the gelling polymer may be provided in a solution whereby an ionic gradient is created between the particle and the solution. Accordingly, the rate of diffusion of multivalent ions from the particle into the gelling polymer solution will be enhanced. For example, the gelling polymer solution may be mixed with a nonionic or low ionic strength solution, to create the ionic gradient between the particle and the alginate solution. Again, a nonionic solution for use in this step may include the sucrose solution described above, for the first wash step. Typically, the nonionic solution will be added to the particle composition prior to addition of the gelling polymer solution. Where a sucrose solution is being used, the concentration of sucrose will generally be from about 5 to about 50% w/v, preferably about 10 to about 30%, before dilution with gelling polymer. Further, the sucrose solution will generally be added to the particles at a volume ratio of from about 0.5:1 to about 2:1 sucrose solution to gelling polymer solution. Preferably, the sucrose solution will be added at a volume ratio of about 1:1 sucrose to gelling polymer. Where alginate is the gelling polymer used, the alginate solution, prior to dilution with sucrose solution, will preferably be provided at a concentration of from about 0.5% to about 4%.

During the coating process, the multivalent ions diffuse from the particle into the surrounding solution of gelling polymer. The interaction between the multivalent ions and the gelling polymer results in the formation of a polymer gel immediately surrounding the particle.

It may be desirable, during the coating process, to dilute the gelling polymer solution further to reduce the viscosity and prevent total gelling of the gelling polymer solution. This may also have the effect of further enhancing the rate of diffusion of multivalent ions from the particles by increasing the osmotic pressure within the growing polymer-gel coated particle.

Because the gelling of the polymer is dependent upon the presence of a particle from which the multivalent ions may diffuse, the production of empty or blank microcapsules may be substantially reduced over other encapsulation methods which rely on the chance incorporation of a particle within an polymer droplet.

Following the overcoating process, the coated material may be washed to remove any free gelling polymer. This wash step may be carried out by any means which will effectively remove the free gelling polymer, e.g., washing with water or a solution containing monovalent ions, e.g., monovalent cations, in the case of alginate, i.e. sodium. Preferably this wash step will be carried out with a monovalent ionic solution. Typically, where alginate is the gelling polymer, a saline solution or saline/sucrose solution is used for this washing step, having a salt concentration of from about 5 mM to about 500 mM, with 125 mM being most preferred, and a sucrose concentration as described above. This washing may also be repeated as desired.

D. Final Gelling of the Polymer Coat

Following the coating process, more complete gelling of the coating layer may be assured by suspending the particles in a second multivalent ion solution. This solution may be the same as that used for the suffusion step or may be another suitable multivalent ionic solution, e.g., $Ca^{++}$ $Ba^{++}$ or $Sr^{++}$, in the case of alginate. This will effectively cure the coating layer and stabilize the gel coating.

Although primarily described in terms of using alginate as the gelling polymer, and divalent cations to cause gelling, it may be appreciated that the methods of the present invention may be practiced using a cationic gelling polymer, e.g. chitin, and a divalent anion to cause gelling, e.g. $SO_4^{-2}$.

Additionally, particles coated using the above described methods may be subjected to additional processing. For example, the coated particles may be further encapsulated using known encapsulation processes, or coated by additional similar or alternative processes. Further, coated particles may be treated with a stabilizing agent or crosslinking polymer to form an outer, semi-permeable membrane. For example, in alginate coatings, the alginate may be coated using polylysine (J. Pharm. Sci. 70:351–354 (1981)) or polyethyleneimine, or alternatively an additional polymer layer of collagen may be added and crosslinked. The entire overcoating process may be repeated where thicker or multiple coatings are desired.

III. Particles to be Coated

A. Generally

The methods of the present invention may generally be used in coating a variety of particle types. The particles for coating will generally be capable of binding or otherwise retaining multivalent ions in some respect, and then releasing or diffusing the divalent ions into the gelling polymer solution. The multivalent ions interact with the gelling polymer to form a stable ion pair, resulting in formation of a polymer gel around the particle.

For example, the particle to be coated may comprise a porous structure whereby the multivalent ions are retained within the particle's pore network. Upon suspension of the particle in the gelling polymer solution, the multivalent ions will diffuse from the pores into the gelling polymer solution. Alternatively, the particle may bind multivalent ions on or within its surface, releasing them upon suspension in a gelling polymer solution. Further, the particle may be able to retain the multivalent ions within a permeable membrane diffusing the ions into the gelling polymer solution via osmotic pressure. This latter example includes particles of biological material, such as cells and tissue fragments, as well as other microcapsule formulations, such as liposomes, alginate microcapsules and coated alginate microcapsules.

B. Biological Material

In preferred aspects, the particles to be coated utilizing the methods of the present invention will comprise biological material. "Biological material" as the phrase is used herein, refers to any material of biological origin which possesses a biological activity. For example, biological material would include cells, i.e., bacterial, mammalian, insect, plant, etc., whether as individual cells or aggregate tissue fragments. Also included within the definition of biological material are proteins, enzymes, cell fragments, organelles, or the like. Biological material coated using the methods of the present invention may be used in a variety of applications, including pharmaceutical, transplant and cell culturing applications.

Although, typically, biological material may be readily coated using the methods of the present invention, occasionally the biological material may be attached to a solid support prior to coating. The support bound material may then be coated with alginate using the methods of the invention. Suitable solid supports include those generally well known in the art, and commercially available, for example, cellulose, agarose, silica, starch, divinylbenzene, polystyrene, or the like. Without being bound to a particular theory, it is believed that the solid support and/or the biological material will bind or incorporate sufficient amounts of divalent cations to allow diffusion of same when suspended in anionic polymer solution, resulting in gel formation around the solid support/biological material composition.

In more preferred aspects, the biological material coated according to the methods of the present invention includes secretory organ tissues for use in transplantation therapy. Transplantation therapy involves the transplantation of tissue from a donor organ to a host, which tissue is intended to replicate the donor organ's function in the host where the host is deficient or lacking in that function.

While the skilled artisan will recognize the utility of the methods of the present invention in coating a variety of tissue types for transplantation, particularly preferred donor organ tissues include pancreatic islet cells, hepatic cells, neural cells, renal cortex cells, vascular endothelial cells, thyroid cells, adrenal cells, thymic cells and ovarian cells.

In a particularly preferred example, the biological material coated according to the methods of the present invention is pancreatic islet cells. Sources of islet cells include, e.g., human, subhuman primate, porcine, bovine, rabbit, rat, mouse and the like, with human and porcine being more preferred. The transplantation of islet cells, and thus, the methods of coating them, may be particularly useful in treating a patient suffering from diabetes mellitus.

C. Overcoating Encapsulated Compositions

1. Generally

Figure 6A:
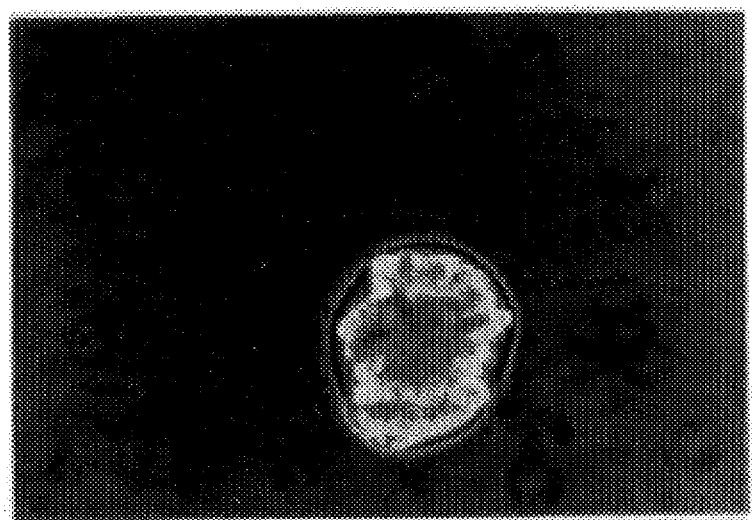
FIGS. 6A–6C show photographs of heart tissue fragments, solution overcoated with an alginate gel using the solution coating methods of the present invention.
Figure 6B:
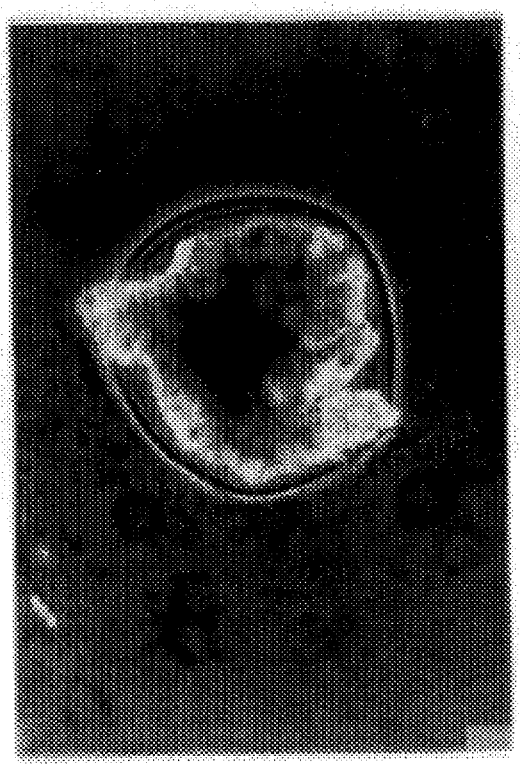
Figure 6C:
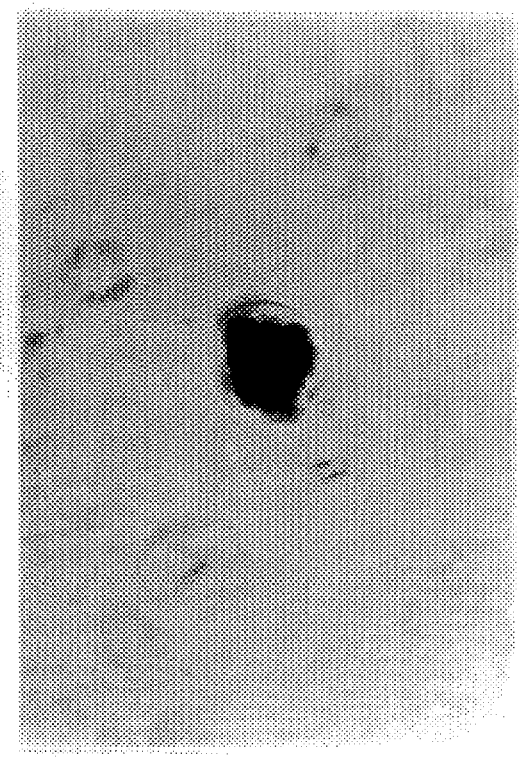
Figure 7A:
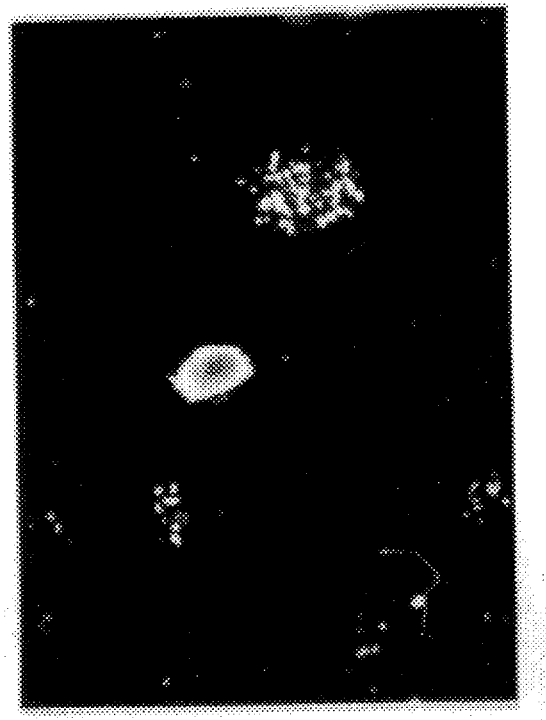
FIGS. 7A–7D show photographs of liver tissue fragments double coated with an alginate gel using the solution coating methods of the present invention.
Figure 7B:
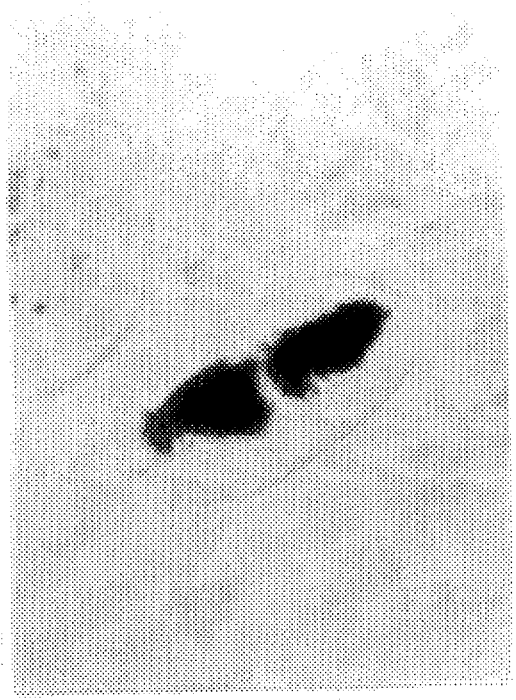
Figure 7C:
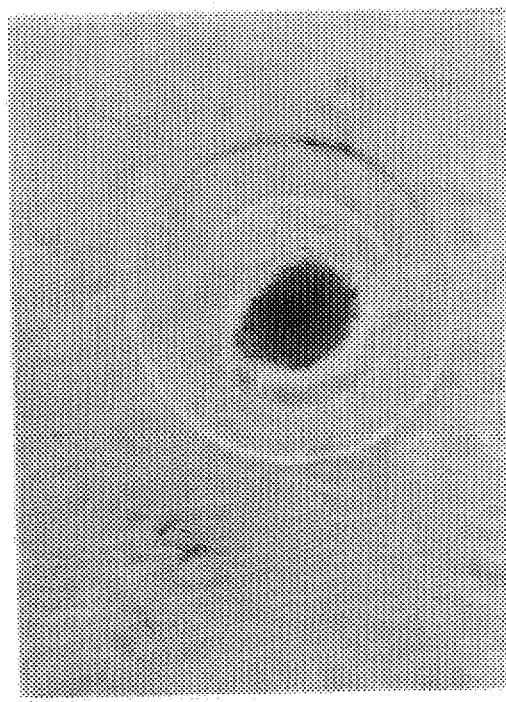
Figure 7D:
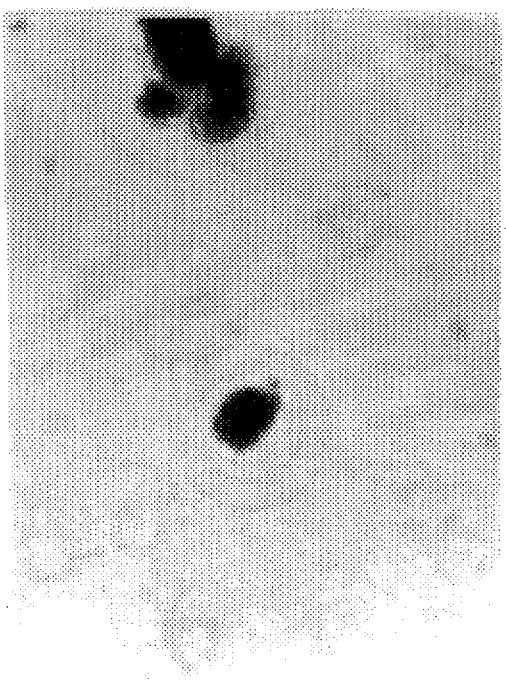

The methods of the present invention have been primarily described in terms of the direct coating of the particle in question. For example, where one wishes to overcoat a sample of tissue, or tissue fragment, that tissue is subjected to the overcoating methods herein described (see, e.g., FIGS. 4, 6 and 7). Such direct overcoating is readily practiced where the material to be coated may bind or incorporate sufficient amounts of multivalent ions during the suffusion step. Directly coated particles may be used in a number of applications, e.g., cell culturing.

In alternative aspects, however, the methods of the present invention may be used to provide additional coating layers to previously encapsulated compositions, or initial layers to compositions which will eventually comprise several layers of coating. This will generally be the case where it is desirable to provide a thicker, more even, and/or more durable coating for the particle in question. For example, in the encapsulation of tissue for transplantation, it is desirable to create a barrier between the transplant and the host's immune system whereby the transplant will be protected from the effects of that immune system. At the same time, the barrier must be of uniform thickness to allow for predictability of performance of the transplant.

The initial encapsulation of the particle may be carried out according to the methods described herein, or alternatively, by one of a number of methods known in the art. For example, a variety of encapsulation compositions may be used, e.g., gelatin, polyvinyl alcohol, ethylcellulose, cellulose acetatephthalate and styrene maleic anhydride (see Remington's Pharmaceutical Sciences, Mack Publishing Co., Easton Pa. (1990)). These encapsulated compositions are then subject to the methods described herein whereby they are overcoated with an additional layer of alginate.

2. Alginate Encapsulated Compositions

In preferred aspects, the particle to be overcoated will be first encapsulated in an alginate gel. Initial alginate encapsulation of the particle to be subsequently overcoated may be carried out by the methods described herein, or by encapsulation methods previously described in the art. These compositions may be further stabilized by, e.g., polylysine, and the like. See J. Pharm. Sci. 70:351–354 (1981), U.S. Pat. Nos. 4,673,566, 4,689,293, 4,789,550, 4,806,355, and 4,789,550.

3. Crosslinked Mixed Functionality Polymer Matrix Coated Particles

In one aspect, encapsulated compositions to be solution overcoated using the methods of the present invention, may comprise a layer of stabilized, crosslinked, mixed functionality polymer. Use of mixed functionality polymer matrices in coating processes is described in substantial detail in U.S. patent application Ser. No. 08/399,295 pending filed concurrently herewith, incorporated herein by reference, for all purposes. The term "Mixed Functionality Polymer" refers to long chain polymeric compounds which possess both positively and negatively charged groups. The mixed functionality, ionic polymers can be characterized by their ability to form fibrous aggregates, and nucleate around macroscopic particles at around neutral pH. In particular, nucleation should occur at from about pH 4.0 to about pH 11.0. Preferably, nucleation should occur at from about pH 5 to about pH 9.0. Examples of mixed functionality polymers include collagen, derivatized collagen, synthetic collagen-like polypeptides, and derivatized polysaccharide polymers which are capable of self assemblage into a macromolecular complex.

The crosslinked, mixed functionality polymer matrix layer results in a stabilized microcapsule which resists such dissolution or degradation. Coating with the crosslinked polymer matrices generally results in a more rigid encapsulation composition than those previously described. These enhanced structural properties result from a more rigid coating polymer, as well as the crosslinking in that polymer. The crosslinking generally provides improved structural characteristics and immune barriers. Crosslinking is discussed in greater detail, below.

An added advantage of the crosslinked polymer matrix layer is the ability to control the porosity of that layer. By controlling the porosity of the layer, the composition may be adjusted depending upon the particular application for which it is to be used, i.e., to exclude or retain molecules of a certain molecular weight. For example, in transplant compositions, the porosity will typically be adjusted to exclude antibodies and/or complement proteins which may damage the transplant. Typically, the porosity will be adjusted so that the layer has restricted diffusion kinetics for molecules larger than 20,000 daltons.

One may adjust the porosity and/or strength of the coating layer by varying the level of polymer matrix coating applied, the level of crosslinking, or by mixing in varying amounts of alternative polymers to promote or detract from the matrix integrity. Stronger mixed functionality polymer matrix layers are generally useful, for example, where the coated material will be exposed to shear or abrasive forces, e.g., in tissue culture vessels.

Examples of stabilized, crosslinked, mixed functionality polymer matrices include various types of collagen. Collagens useful as mixed functionality polymer matrix layers, will generally be capable of self assemblage. Preferably, this self assemblage will occur at or around neutral or relevant pH. The "relevant pH" may vary depending upon the nature of the biological material to be encapsulated or the biological environment into which the composition is to be introduced. For example, in most mammalian applications, the relevant pH will be approximately neutral. However, where the material to be coated is not amenable to pH outside either the basic or acidic range, it may be desirable to use a collagen which will allow coating in this range. Similarly, where the environment into which the composition is to be introduced is within the acidic or basic range, it may be desirable to provide a collagen coating which will remain insoluble within this range.

Although acid soluble collagen types are generally used in mixed functionality polymer matrices, those of skill in the art will recognize that a number of collagen forms may be used. For example, U.S. Pat. No. 4,164,559 to Miyata, et al., reports the alteration of the fibril formation pH profile by varying the derivatization of the collagen. The collagen forms therein described may be applicable where the relevant pH for a particular encapsulated composition is lower or higher than the neutral range.

As with many soluble proteins, the solubility of various collagen types is dependent upon a number of factors, including pH, temperature, molecular weight of the predominant form of collagen present, protein concentration and salt concentration in the solution. Another factor affecting solubility can be the presence of particulate matter in the solution. Such particulate matter can become a site of nucleation for proteins which are moderately soluble. Without being bound to a particular theory, it is believed that the material to be coated using the methods described herein provides such a macroscopic nucleation site for the collagen.

Accordingly, the mixed functionality polymer matrix layer may be prepared by taking advantage of the natural properties of the polymer solution used. In particular, biological material, whether encapsulated, support bound or a free particulate, is introduced into a solution of the mixed functionality polymer. The conditions of the solution may be adjusted whereby the polymer begins to form into fibrils, and nucleate around the biological material. For example, in the case of collagen, the pH, salt concentration, temperature and/or the concentration of collagen may be selected or adjusted to control the initiation rate, extent and quality of fibril formation. The particular conditions adjusted and the range of these adjustments may depend upon a number of factors, including, for example, the sensitivity of the material to be encapsulated to changes in pH, temperature and salt concentration.

Conditions of nucleation may vary depending upon the application for the particular coated material. For example, nucleation may be affected by varying the pH, organic and inorganic salt concentration, as well as the concentration of mixed functionality polymer during the nucleation step. These nucleation conditions are discussed in substantial detail in U.S. patent application Ser. No. 08/399,295, pending filed concurrently herewith.

In addition to adjusting the conditions of nucleation, it may also be desirable to adjust the level of mixed functionality polymer coating applied to the biological material. Because the amount of coating is related to the surface area of the material to be coated, the amount of total polymer added in the coating process will likely vary depending upon the nature of the material to be coated. For example, where coating with collagen as the mixed functionality polymer, where the material to be coated comprises small particles, e.g., alginate microcapsules or beads, ranging in size from about 50 to about 250 μm in diameter, the collagen may be added at from about 0.2 to about 2.0 ml of 0.3 wt % collagen solution per ml packed bead volume. For larger size particles, or a thinner collagen coating, lower levels of total collagen may be added, while a thicker coating or smaller particle sizes (having greater surface area per ml packed bead volume) may utilize more total added collagen.

The mixed functionality polymer matrix may be further adjusted through the addition of alternative polymers, added concurrently with the mixed functionality polymer, which enhance, or alternatively, detract from the integrity and thus the porosity of the resulting matrix. For example, additional crosslinkable polymers may provide a substantial enhancement to the integrity of the matrix, much like interlocking puzzle pieces. Alternatively, the integrity of the matrix may be reduced by the inclusion of polymers which act as spacers between the mixed functionality polymer fibrils reducing the level of crosslinking.

Generally, where collagen is the mixed functionality polymer, collagen solutions will be in a dilute acetic acid solution at about pH 4.5 (deionized water adjusted to pH 4.5 with acetic acid). At pH 4.5, the collagen solution will generally be somewhat viscous due to preassembly of the fibrils. Adjustment of the pH of the collagen solution to greater than pH 5 results in fibril formation and polymer nucleation. The nucleation of collagen at around neutral pH makes it particularly suitable for coating biological materials which are sensitive to extremes of pH. Therefore, typically, the initiation of collagen nucleation is carried out by adjusting the pH of the collagen solution to greater than about pH 4. Preferably, the pH is adjusted to between about pH 5 and pH 8.0, and most preferably, from about pH 6.5 to about pH 6.9.

Collagen proteins have a reported isoelectric point of between about 8.5 and 10. Thus, at nucleation pH, e.g., between 5 and 8, the collagen peptides will generally carry a net positive charge. Accordingly, it will be appreciated that in preferred methods, the biological material to be coated may carry a net negative charge. The differences in net charges between the collagen and the material around which nucleation is desired may enhance nucleation around the biological material.

Collagens which may be used as mixed functionality polymer matrices include commercially available collagen types, as well as derivatized collagen. Protein derivatization is well known in the art, and may allow for the alteration of the properties of the particular protein used, e.g., improved nucleation, better stability of crosslinked forms, alteration of nucleation pH profiles etc. Examples of derivatized collagen include pegylated collagen (collagen to which polyethylene glycol has been covalently attached), succinylated collagen, alkylated collagen (e.g., methylated), aminated collagen, activated aldehyde derivatized collagen, and the like. See, e.g., U.S. Pat. No. 4,164,559.

Although the discussion of mixed functionality polymer matrices is primarily in terms of a collagen coating, it may also be appreciated that a variety of other polymers may be used. For example, polymers which possess similar characteristics to the collagen compositions just described may be particularly useful. Of particular interest are those polymers which are soluble in the acidic pH or basic pH, but precipitate at around neutral or relevant pH. More preferred would be those polymers which have a net charge opposite to the material being coated, at neutral pH.

In another aspect, the stabilized crosslinked polymer matrix may comprise a derivatized polysaccharide polymer, preferably an alginate polymer. Such derivatized alginate polymers are characterized by mixed anionic and cationic groups within each polymer chain, similar to the alternating charges of the collagen molecules. Derivatization of polymers and polysaccharides may be carried out by methods generally well known in the art.

Following the application of the polymer matrix layer, the layer may be crosslinked to stabilize that layer. The type of crosslinker used will generally depend upon the type of polymer used in the coating process. Zero-length crosslinkers are preferred for the practicing of the present invention. A "zero-length crosslinker" refers to a crosslinking compound which will mediate or produce a direct crosslink between functional groups of two polymer molecules. For example, in the crosslinking of two proteins, a zero-length crosslinker will result in the formation of a bridge, or crosslink between a carboxyl group from an amino acid sidechain of one protein, and an amino group of another, without integrating foreign material or leaving exogenous adducts. Particularly useful crosslinkers effect the crosslinking via a condensation reaction liberating water, ammonia or an amine containing compound, an alcohol or other simple group. Such crosslinkers are termed condensable crosslinkers.

In some aspects of the present invention, where collagen is the crosslinked, mixed functionality polymer matrix of choice, a number of organic crosslinkers, well known in the art may be used, e.g., carbodiimides. While organic soluble crosslinkers may be used so long as the solvent effects can be tolerated by the biological material, in a more preferred aspect, the crosslinking of the collagen layer is carried out using a water soluble crosslinker, e.g., 1-ethyl-3-(3-dimethylaminopropyl)carbodiimide hydrochloride ("EDC").

The level of crosslinking may be adjusted to vary the strength, and/or the porosity of the layer. Alternatively, additional polymers may be added to the layer to enhance or detract from the integrity of the crosslinked collagen coating layer.

Thus, a variety of materials may be overcoated using the methods of the present invention, including free, encapsulated or support bound biological material. Because the methods of the present invention rely upon the diffusion of divalent cations from the particle into the solution of anionic polymer, the need for extraneous droplet generation devices is obviated. Accordingly, the entire overcoating process of the present invention can be carried out in solution.

The present invention is further illustrated by the following examples. These examples are merely to illustrate aspects of the present invention and are not intended as limitations of this invention.

EXAMPLES

Example 1
Alginate Solution Overcoating Process

The alginate overcoating process described below was applied to red blood cells which had been first encapsulated in alginate using an ES droplet generator, followed by a coating of crosslinked collagen. These microcapsules, or "beads", were then solution overcoated with an additional layer of alginate gel.

Polypropylene test tubes (5 and 15 ml) and a 3 ml transfer pipet were coated with 0.5% gelatin, 125 mM saline, 10 mM N-2-Hydroxyethylpiperazine-N'-2-ethanesulfonic acid ("HEPES") at pH 7.2, and allowed to drain dry. The beads were aliquoted into the 5 ml polypropylene test tubes where the beads were allowed to settle. Beads were added or subtracted to yield a settled bead volume of approximately 0.3 ml. The supernatant was removed from the settled beads. The tube was then filled with 2.5 mM $BaCl_2$, 125 mM saline, 10 mM HEPES at pH 7.2, and the beads were incubated on a LabQuake™ rotator for 1 hour at room temperature. The beads were again allowed to settle for 5 to 10 minutes followed by centrifugation at 1000–1500 rpm for 30 seconds, and the supernatant was removed down to 0.4–0.5 mls. The tube was then filled with a solution of 25% sucrose, 2.5 mM $BaCl_2$, 125 mM NaCl, 10 mM HEPES, pH 7.2, and mixed by inversion and again rotated for 1 hour at room temperature. The beads were then allowed to settle for 5 minutes, centrifuged at 1000–1500 rpm for 30 seconds and the supernatant was removed. This step was repeated as necessary (generally 3 times). The tube was then filled with a solution of 25% sucrose, 125 mM NaCl, 10 mM HEPES, pH 7.2, and mixed by inversion, followed by immediate centrifugation as above. This step was repeated. 0.75 ml of sucrose/saline/HEPES solution was added to disturb the bead pellet, followed by careful addition of 2.5 mls of 2.8% sodium alginate in 125 mM saline, 10 mM HEPES pH 7.2. The beads were then immediately mixed by vigorous shaking of the test tube for 3 seconds followed by gentle inversion or rotation for 3 minutes. The bead suspension was transferred to a 15 ml polypropylene test tube, and the 5 ml tube was rinsed with the sucrose/saline/HEPES solution until the 15 ml tube was filled. This tube was mixed by inversion several times, and centrifuged. The majority of the supernatant was removed, and sucrose/saline/HEPES solution was added to bring the volume of the suspension to 8 mls. 6 mls of sucrose/$BaCl_2$/saline/HEPES was then added and the solution was mixed by inversion and rotated for 5 minutes. The beads were settled, centrifuged and the supernatant decanted. The beads were then stabilized by adding 6 mls of $BaCl_2$/saline/HEPES solution to the bead pellet which was mixed, rotated, centrifuged and decanted. This step was repeated. The resulting beads were analyzed microscopically. Photographs of resulting alginate overcoated beads are shown in FIG. 3A-1 through 3A-3 and 3B-1 through 3B3.

Figure 8A:
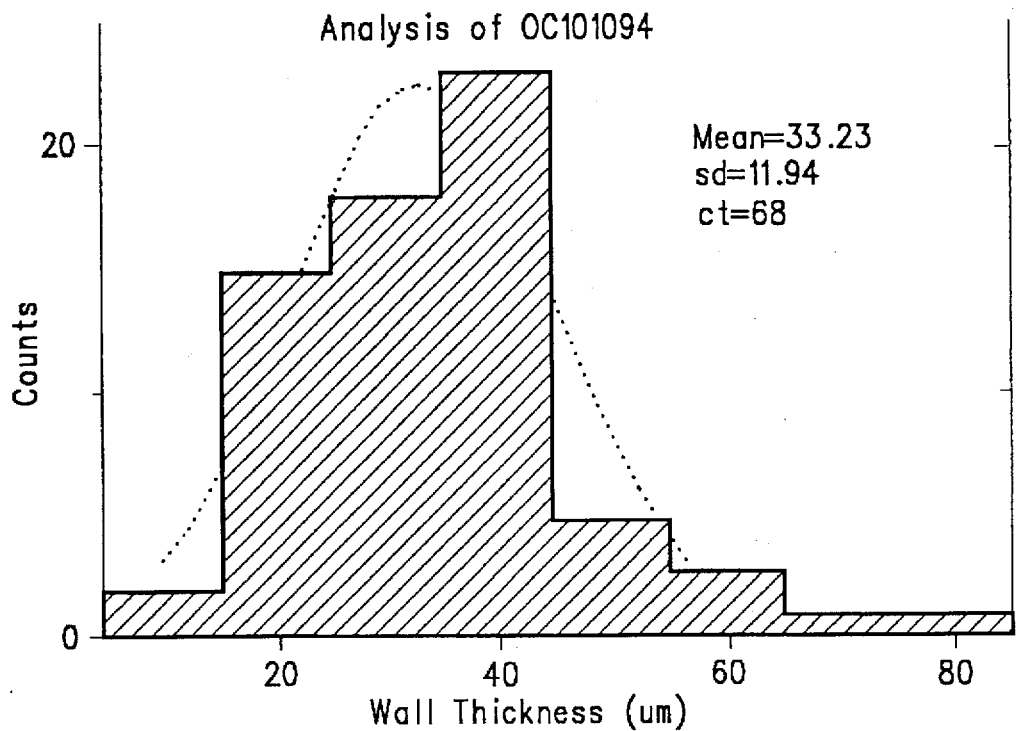
FIGS. 8A and 8B are bar graphs showing the population distribution of wall or coating thickness of two samples of microcapsules, overcoated according to the methods of the present invention. The mean coating thickness from the two lots were 33.23 µm and 31.44 µm, respectively.
Figure 8B:
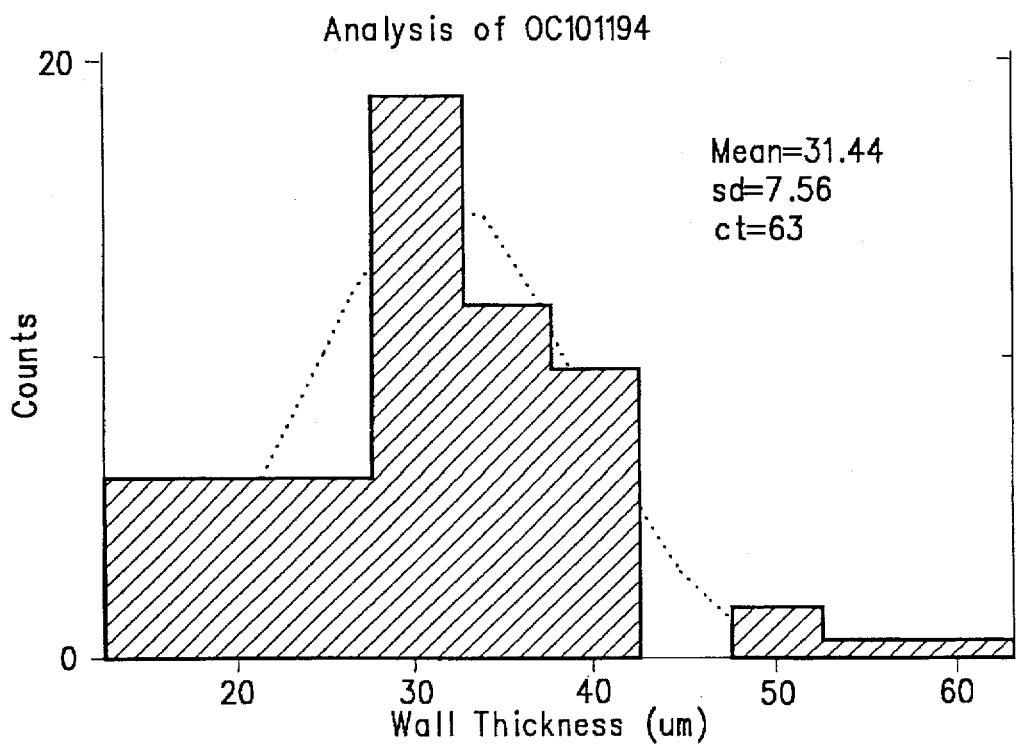
Figure 9:
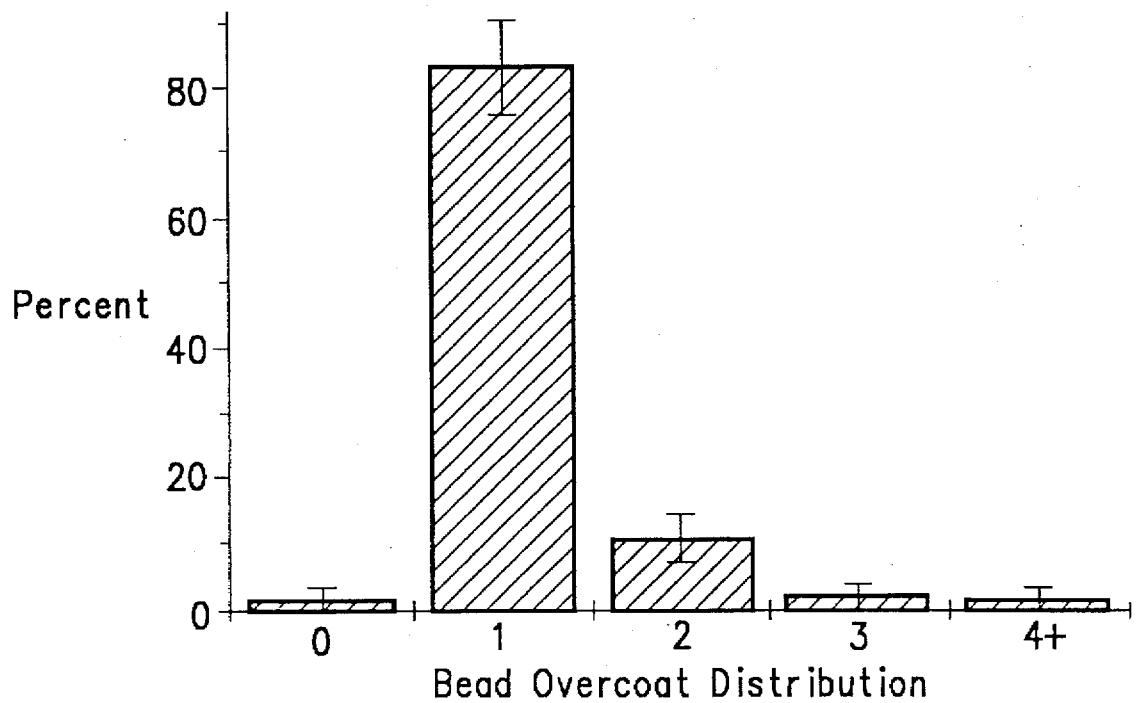
FIG. 9 is a bar graph showing the population distribution of alginate encapsulated red blood cells which have been overcoated using the methods of the present invention. Shown is the distribution of beads as singlets ("1"), doublets ("2"), triplets ("3") and uncoated beads ("0").

Upon completion of the process, a representative sample of overcoated beads was analyzed by microscopic evaluation. Several fields of view are counted to determine the population distribution of overcoated beads. The distribution of singlet beads (1), doublets (2), triplets (3) and uncoated beads (0), is shown in FIGS. 8A and 8B. Also shown are aggregates of 4 or more beads (4+). As shown, greater than 90% of the beads prepared represent coated singlet or doublet beads, while uncoated beads represent a small minority of the total population.

Although described as overcoating a particular particle type, this same method was also applied to alternative materials, as shown in Examples 3–5.

Example 2
ES Encapsulated Islets, Double Coated Using Laminar Air Flow Extrusion Device Pancreatic islet cells were double encapsulated using an electrostatic ("ES") droplet generation apparatus for the first encapsulation step, followed by a second encapsulation using a laminar air flow extrusion device. The islets were first encapsulated using an ES droplet generator, and collected in Calcium chloride ("$CaCl_2$"). The resulting alginate encapsulated islets were then subjected to a second encapsulation using a laminar air-flow extrusion apparatus and method as follows:

The suspension of encapsulated pancreatic islets in alginate is placed in a syringe barrel. The syringe plunger is displaced to provide a flow rate of 0.3 ml/min to dispense the cell suspension/alginate solution from the needle while air is delivered to the outer sleeve of the apparatus at an entry pressure of about 30 psi. Droplets of the suspension were collected in a vessel containing 120 mM $CaCl_2$ and 10 mM HEPES buffer. The vessel is positioned so that the $CaCl_2$ solution is about 160 to 165 mm from the tip of the needle.

Example 3
Single Coated Islet Cells Solution Overcoated with Alginate

For this example, alginate encapsulated islet cells were used for solution overcoating with an additional layer of alginate. The islet cells were first encapsulated in a single Ca-alginate microcapsule using the electrostatic droplet generation method described in Example 2.

Figure 2A:
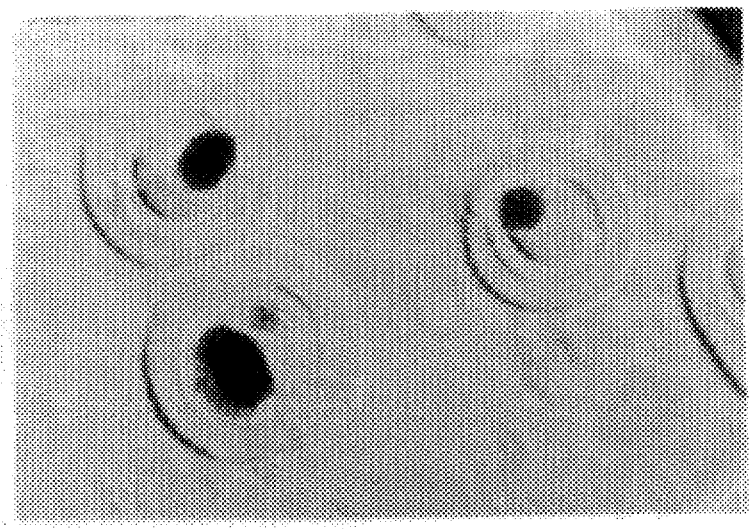
FIGS. 2A–2C shows photographs of islet cell clusters, first encapsulated in an alginate gel using an electrostatic droplet generator apparatus, then overcoated with alginate using the solution coating methods of the present invention.
Figure 2B:
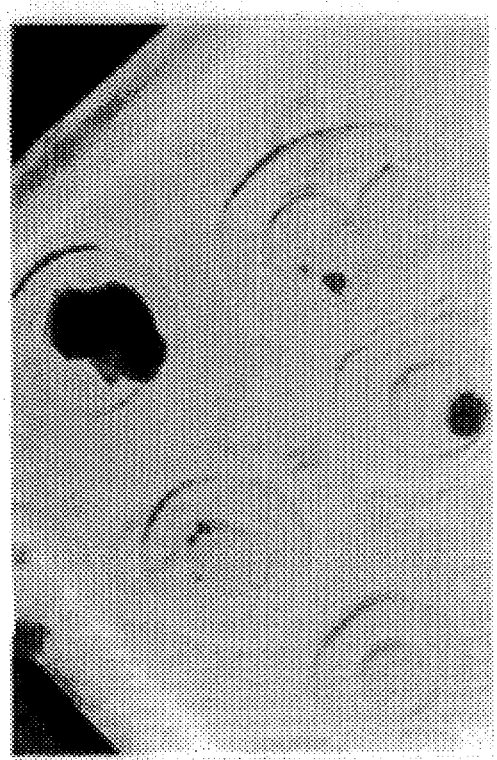
Figure 2C:
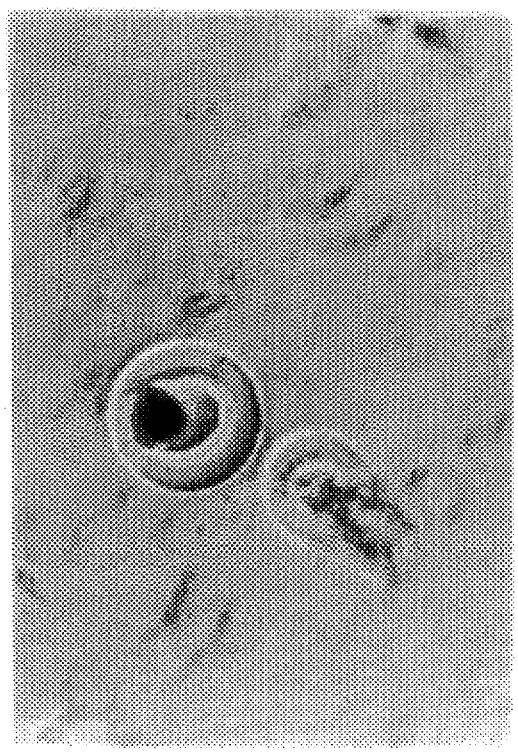
Figures 1, 3A:
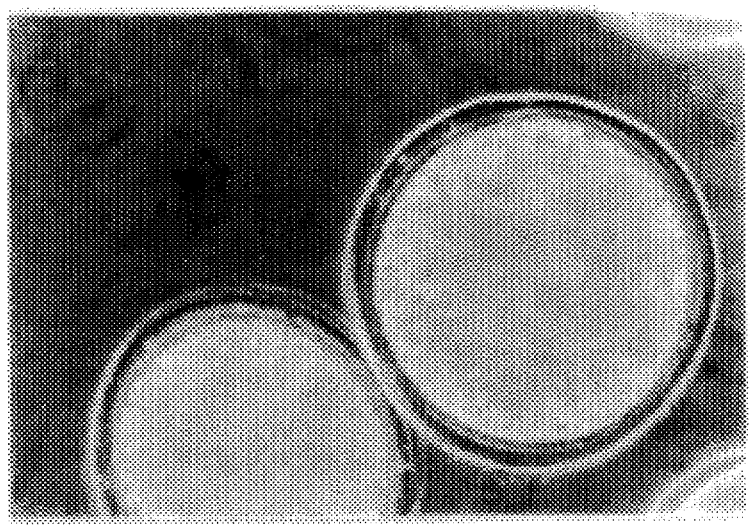
FIGS. 3A-1 through 3A-3 and 3B-1 through 3B-3 show photographs of red blood cells, first encapsulated in alginate using an ES droplet generator, then coated with collagen which was then crosslinked and followed by an overcoating of alginate gel using the solution coating methods of the present invention.
Figures 2, 3A:
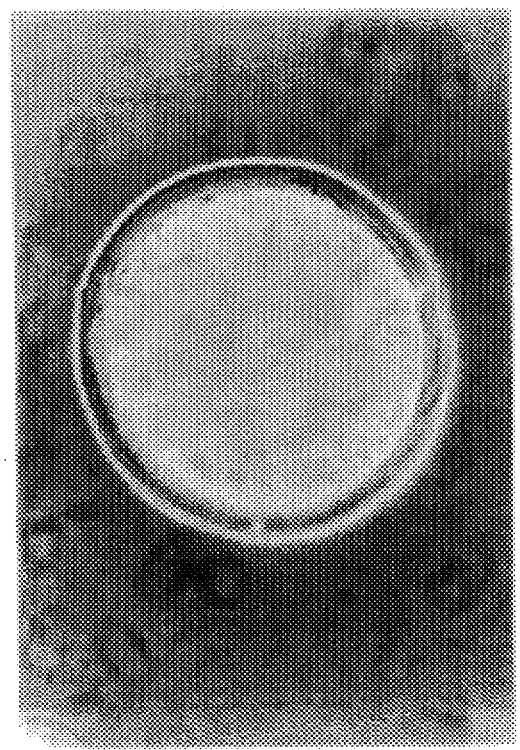
Figures 3, 3A:
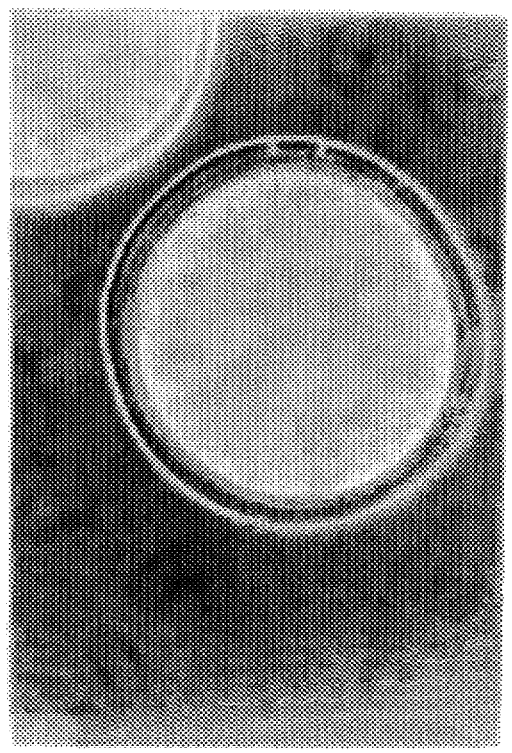
Figures 1, 3B:
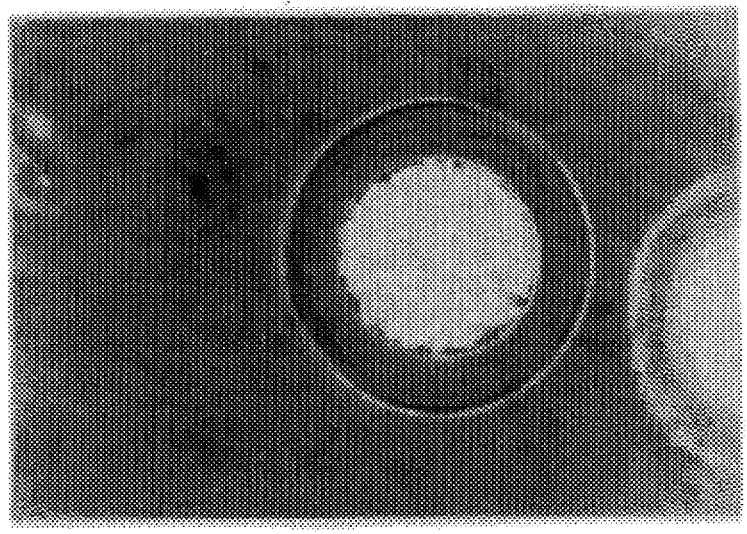
Figures 2, 3B:
Figures 3, 3B:
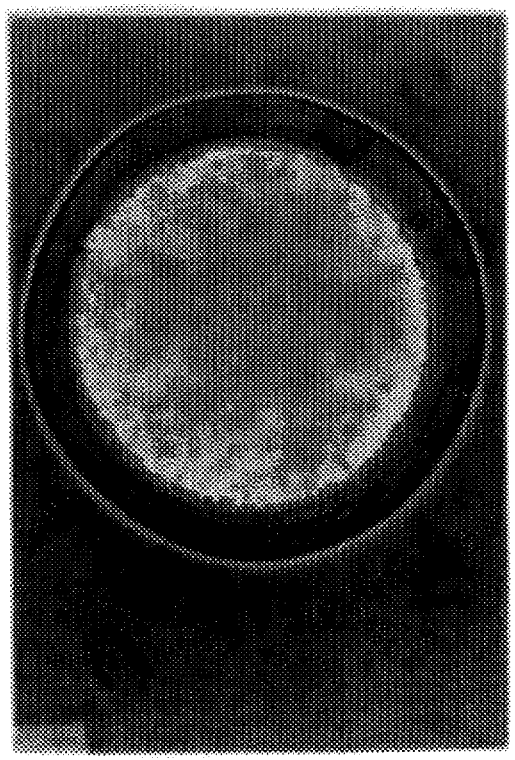
Figure 4A:
FIGS. 4A–4D show photographs of pancreatic tissue fragments, solution overcoated with an alginate gel using the solution coating methods of the present invention.
Figure 4B:
Figure 4C:
Figure 4D:
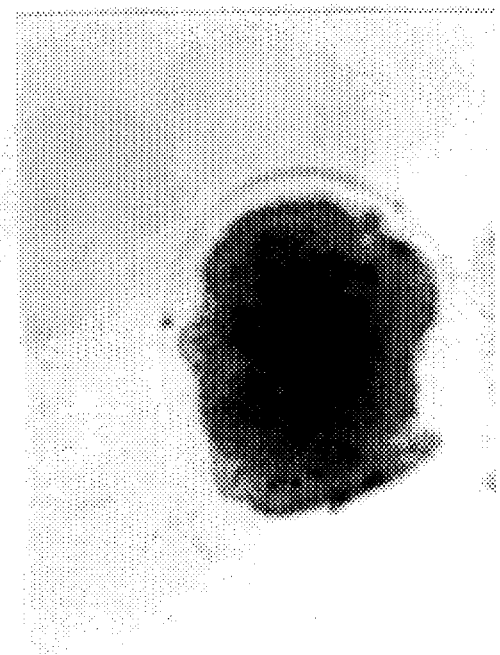
Figure 5A:
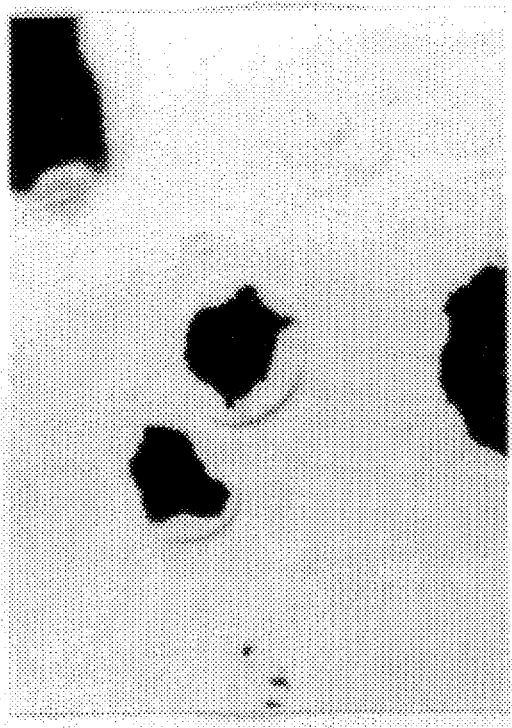
FIGS. 5A–5D show a photograph of a charcoal particles coated with an alginate gel using the solution coating methods of the present invention.
Figure 5B:
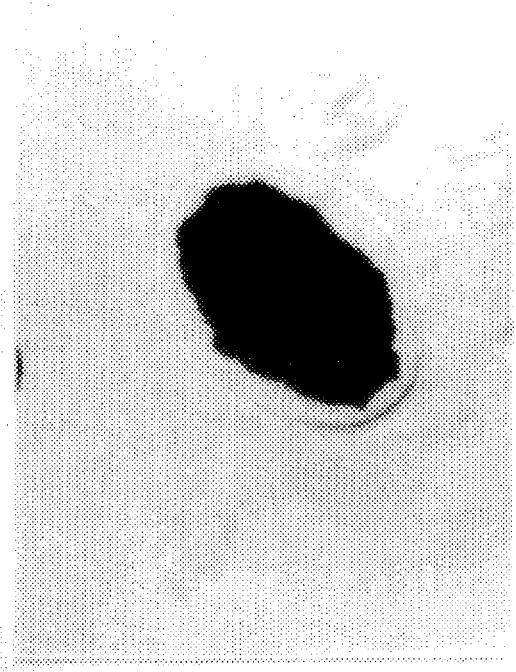
Figure 5C:
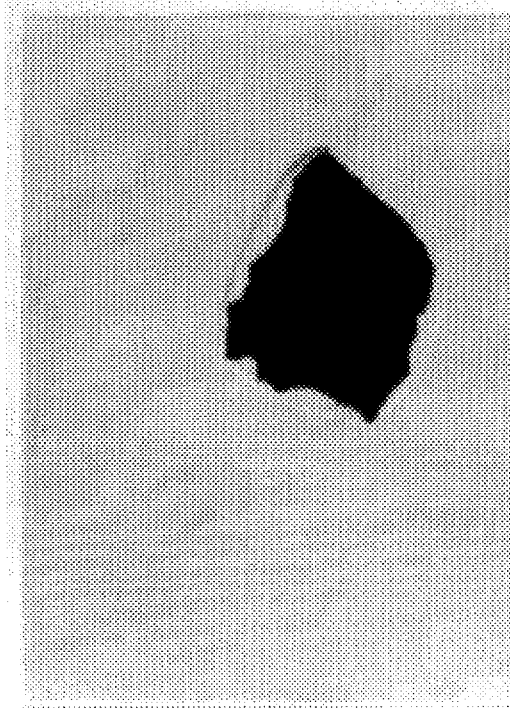
Figure 5D:

The alginate encapsulated islets were overcoated with an additional layer of alginate using the solution overcoating method of Example 1. The resulting alginate overcoated, alginate encapsulated islet cells are shown in FIGS. 2A–2C. The alginate overcoating, shown as the outer layer illustrates a more uniform thickness than encapsulated islets prior to overcoating.

Example 4
Solution Overcoated Tissue Fragments

For this example, pancreatic tissue fragments, heart tissue fragments and liver tissue fragments were suffused with $BaCl_2$ and solution overcoated with alginate according to the method of Example 1 (shown in FIGS. 4A–4D, 6A–6C and 7A–7D respectively). Tissue fragments solution coated with alginate are shown to have a uniform layer of alginate surrounding the tissue. This demonstrates that larger material fragments, and fragments of irregular shape can be coated according to the methods of the present invention. Traditional encapsulation methods are somewhat limited in this respect.

Example 5
Solution Overcoated Charcoal Particle

Charcoal fragments were also coated according to the solution overcoating method of Example 1 (shown in FIGS. 5A–5D). Coating of the charcoal particle, a porous composition, demonstrates the efficacy of the coating methods of the present invention in coating other porous compositions, e.g., solid supports, and the like.

While the foregoing invention has been described in some detail for purposes of clarity and understanding, it will be clear to one skilled in the art from a reading of this disclosure that various changes in form and detail can be made without departing from the true scope of the invention. All publications and patent documents cited in this application are incorporated by reference in their entirety for all purposes to the same extent as if each individual publication or patent document were so individually denoted.

What is claimed is:

1. A method of solution over-coating a particle with a gelling polymer, said method comprising:

suffusing said particle with a solution of multivalent ions;

washing said particle to remove free multivalent ions on the surface of said particle;

suspending said particle in a solution of gelling polymer, whereby said multivalent ions diffuse from said particle into said solution of gelling polymer, thereby gelling a coating of said solution of gelling polymer on the surface of said particle to form a solution over-coated particle; and recovering said solution over-coated particle from said solution of gelling polymer, wherein said solution overcoated particle is from about 3 µm to about 2 mm in diameter, and wherein said method does not employ a droplet generation device.

2. The method of claim 1, wherein said gelling polymer is alginate, and said solution of multivalent ions is a solution of divalent cations.

3. The method of claim 1, wherein said particle comprises biological material.

4. The method of claim 3, wherein said biological material is cells.

5. The method of claim 4, wherein said cells are first encapsulated in a matrix.

6. The method of claim 5, wherein said matrix comprises an alginate gel.

7. The method of claim 6, wherein said matrix further comprises a layer of crosslinked mixed functionality polymer matrix with a defined matrix porosity.

8. The method of claim 7, wherein said crosslinked, mixed functionality polymer matrix comprises crosslinked collagen.

9. The method of claim 2, wherein said solution of divalent cations comprises divalent cations selected from the group consisting of $Ba^{++}$, $Ca^{++}$, $Sr^{++}$ and $Fe^{++}$.

10. The method of claim 9, wherein said solution of divalent metal cations comprises $Ba++$.

11. The method of claim 4, wherein said cells are pancreatic islets.

12. The method of claim 9, wherein said solution of divalent cations comprises $Sr^{++}$.

13. A method of solution over-coating islets with a gelling polymer, said method comprising:

suffusing said islets with a solution of multivalent ions;

washing said islets to remove free multivalent ions on the surface of said islets;

suspending said islets in a solution of gelling polymer, whereby said multivalent ions diffuse from said islets into said solution of gelling polymer, thereby gelling a coating of said solution of gelling polymer on the surface of said islets to form a solution over-coated islets; and recovering said solution over-coated islets from said solution of gelling polymer, wherein said method does not employ a droplet generation device.

14. A method of solution over-coating mammalian tissue with a gelling polymer, said method comprising:

suffusing said mammalian tissue with a solution of multivalent ions;

washing said tissue to remove free multivalent ions on the surface of said mammalian tissue;

suspending said mammalian tissue in a solution of gelling polymer, whereby said multivalent ions diffuse from said mammalian tissue into said solution of gelling polymer, thereby gelling a coating of said solution of gelling polymer on the surface of said mammalian tissue to form solution over-coated mammalian tissue; and recovering said solution over-coated mammalian tissue from said solution of gelling polymer, wherein said method does not employ a droplet generation device.

15. A method of solution over-coating a particle with a gelling polymer, said method comprising:

suffusing said particle with a solution of multivalent ions;

washing said particle with a nonionic solution to remove free multivalent ions on the surface of said particle;

suspending said particle in a solution of gelling polymer, whereby said multivalent ions diffuse from said particle into said solution of gelling polymer, thereby gelling a coating of said solution of gelling polymer on the surface of said particle to form a solution over-coated particle; and recovering said solution over-coated particle from said solution of gelling polymer, wherein said method does not employ a droplet generation device.

* * * * *